US005695973A

United States Patent [19]
Subbiah

[11] Patent Number: 5,695,973
[45] Date of Patent: Dec. 9, 1997

[54] ISOLATED ALCOHOL DEHYDROGENASE PRODUCING MOLD

[75] Inventor: Ven Subbiah, Edenton, N.C.

[73] Assignee: R.J. Reynolds Tobacco Company, Winston-Salem, N.C.

[21] Appl. No.: 674,920

[22] Filed: Jul. 3, 1996

[51] Int. Cl.$^6$ .................................. C12P 7/02; C12N 1/00
[52] U.S. Cl. ........................ 435/155; 435/134; 435/911; 435/254.1; 426/52
[58] Field of Search ................................. 435/155, 134, 435/911, 254.1; 426/52

[56] References Cited

U.S. PATENT DOCUMENTS

| | | | |
|---|---|---|---|
| 3,839,457 | 10/1974 | Jouffret | 260/601 |
| 3,962,354 | 6/1976 | Dahil, Jr. | 260/638 |
| 4,769,243 | 9/1988 | Kanisawa et al. | 426/33 |
| 4,806,379 | 2/1989 | Goers et al. | 426/650 |
| 5,017,386 | 5/1991 | Hildebrand et al. | 426/18 |
| 5,464,761 | 11/1995 | Muller et al. | 435/147 |

FOREIGN PATENT DOCUMENTS

| | | |
|---|---|---|
| 89 12901 | 4/1991 | France . |
| 93/24644 | 12/1993 | WIPO . |

OTHER PUBLICATIONS

Pelczar et al., Fungi: the Molds, In: Microbiology, 4th edition, McGraw-Hill Book Company, pp. 285–301, 1977.
Charton et al., Specifities of immobilized Geotrichum candidum CMICC 335426 lipases A and B in hydrolysis and ester sysnthesis reactions in organic solvents, Enzyme Microb. Technol., vol. 15, pp. 489–493, 1993.
H.W. Gardner, "Flavors and Bitter Tastes from Oxidation of Lipids by Enzymes," in *Flavor Chemistry of Fats and Oils*, 189–206 (eds. D.B. Min and T.H. Smouse, 1985).
J. Sekiya et al., "Seasonal Changes in Activities of Enzymes Responsible for the Formation of $C_6$–aldehydes and $C_6$–alcohols in Tea Leaves, and the Effects of Environmental Temperatures on the Enzyme Activities," *Plant Cell. Physiol.* 25(2)269–280 (1984).
Sigma Catalog, p. 74 (1992).
The New Royal Horticultural Society Dictionary of Gardening vol. 1, 144–145 (ed. A. Huxley, 1992).
J.M. Olias et al., "Aroma of Virgin Olive Oil: Biogenesis of the Green Odor Notes," *J. Agric. Food Chem.* 41, 2368–2373 (1993).
D.R. Phillips et al., "Partial Purification and Properties of a Cis–3:Trans–2–Enal Isomerase From Cucumber Fruit," *Phytochemistry* 18, 401–404 (1979).
J. Sekiya et al., "Cis–3–Hexenal and n–Hexanal Formation From Linolenic And Linoleic Acids in Alfalfa Cells Cultured In Vitro," *Plant Science Letters* 19, 165–169 (1977).
B.O. de Lumen et al., "Formation of Volatile Flavor Compounds In Green Beans From Linoleic Acid and Linolenic Acids," *J. Food Sci.* 43(3), 698–702 (1978).
J. Sekiya et al., "Fatty Acid Hydroperoxide Lyase in Tobacco Cells Cultured In Vitro," *Phytochemistry*, 23(11), 2439–2443 (1984).

T.W. Pfeiffer et al., "Inheritance of a Lipoxygenase–1 Allozyme in Soybean," *Crop. Sci.* 33, 691–693 (1993).
A. Hatanaka et al., "Distribution of and Enzyme System Producing cis–3–Hexenal and n–Hexenal From Linoleic and Linoleic Acids in Some Plants," *Phytochemistry* 17, 869–872 (1978).
A. Hatanaka et al., "Fatty Acid Hydroperoxide Lyase in Plant Tissues," in American Chemical Society, *Biogeneration of Aromas*, 167–75 (1986).
A. Hatanaka, "Biosynthesis of Leaf Alcohol," *Bull. Inst. Chem. Res.*, 61(2) 180–192 (1983).
J. Sekiya et al., "Distribution of Lipoxygenase and Hydroperoxide Lyase in the Leaves of Various Plant Species," *Phytochemistry* 22(9), 1867–1869 (1983).
E. Gotz–Schmidt et al., "$C_6$ Volatiles in Homogenates from Green Leaves: Localization of Hydroperoxide Lyase Activity," *Lebensm–Wiss Technol.* 19(2), 152–155 (1986).
A.J. McLeod et al., "Formation of (E)–Hex–2–enal and (Z)–Hex–3–en–1–ol by Fresh Leaves of *Brassica oleracea*," *J. Agric. Food. Chem.* 27(3), 469–75 (1979).
R. Saijo et al., "Increase of Cis–3–Hexen–1–ol Content in Tea Leaves Following Mechanical Injury," *Phytochemistry* 14, 181–182 (1975).
E.J. Stone et al. "Formation of Aldehydes and Alcohols in Tomato Fruit From U–$^{14}$C–Labeled Linolenic and Linoleic Acids," *J. Food. Sci.* 40, 1138–1141 (1978).
A. Hatanaka et al., "Alcohol Dehydrogenase from *Thea sinensis* Seeds," *Agr. Biol. Chem.* 38(10), 1835–1844 (1974).
A. Hatanaka et al., "Formation of Cis–3–Hexenal, Trans–2–Hexenal and Cis–3–Hexenal In Macerated *Thea sinensis* Leaves," *Phytochemistry* 12, 2341–2346 (1973).
A. Hatanaka et al., "Purification and Properties of Alcohol Dehydrogenase from Tea Seeds," *Agr. Biol. Chem.* 36(11), 2033–2035 (1972).
A. Hatanaka et al., "Phytochemical Isomerization of Leaf Aldehyde," *Agr. Biol. Chem.* 36(7), 1263–1264 (1972).
R.T. Major et al., "Formation of 2–Hexenal From Linolenic Acid By Macerated Ginkgo Leaves," *Phytochemistry* 11, 611–617 (1972).

*Primary Examiner*—Leon B. Lankford, Jr.
*Assistant Examiner*—Christopher R. Tate
*Attorney, Agent, or Firm*—Myers Bigel Sibley & Sajovec, LLP

[57] ABSTRACT

The present invention relates to a microorganism capable of producing alcohol dehydrogenase (ADH). The microorganism of the invention is a non-yeast mold obtained from the kale plant. In a preferred embodiment of the invention, the mold is *Geotrichium candidum* IMI 369326. The microorganism of the invention is particularly useful in the green note processing industry as a substitute for yeast. For example, the microorganism is useful as a substitute for yeast in a process of converting a leaf aldehyde to a leaf alcohol.

11 Claims, No Drawings

ISOLATED ALCOHOL DEHYDROGENASE PRODUCING MOLD

FIELD OF THE INVENTION

The present invention relates to an isolated microorganism, and more specifically to an isolated mold useful in producing green note compounds.

BACKGROUND OF THE INVENTION

Leaf alcohol (i.e., cis-3-hexen-1-ol) and leaf aldehyde (i.e., trans-2-hexenal) are present in a wide variety of fresh leaves, vegetables and fruits. These compounds are responsible for a so-called "green aroma," "green odor," "fresh note," or "green note." Related compounds present in many plants include trans-2-hexenol, cis-2-hexenol, trans-3-hexenol, 1-hexenol, 1-hexenal, and cis-3-hexenal. Green note compounds and uses thereof are set forth by Morris, *Perfumer & Flavorist*, Vol. 6, No. 1 (1981) and Clark, *Perfumer and Flavorist*, Vol. 15 (1990). Green note compounds exhibit organoleptic characteristics which can be characterized as fresh or grassy in nature. Such compounds can be used to sharpen and enhance flavored products, such as those products having fruit flavors.

Green note compounds have been isolated from plants or chemically synthesized, as reported by Bedoukian, *Amer. Perf.* 78, 31 (1963) and U.S. Pat. No. 3,839,457 to Jouffret. Green note compounds are present in plant essential oils (e.g., sage, citrus, and mint) and have been obtained by steam distillation of plant material followed by fractional distillation or "topping" techniques. Green note compounds have also been biosynthetically produced, as reported by Muller et al., *Adv. Flav. Res. Tech. Symposium* (1993); Hatanaka et al., *Phytochem.* 17, 869 (1978); Lumen et al., *J. Food Sci.* 43, 698 (1978); and U.S. Pat. Nos. 4,769,243 to Kaniswa et al. and 4,806,379 to Goers et al.

One green note-producing biosynthetic reaction involves the unsaturated C-6 hydroperoxydismutation of linolenic acid and is carried out using a series of enzymatic steps. In particular, lipoxygenase forms a hydroperoxide moiety at a double bond of a fatty acid (e.g. linolenic acid). The enzyme hydroperoxide lyase cleaves the hydroperoxide to produce a C-6 unsaturated aldehyde, in particular, cis-3-hexen-1-al. Aldehyde isomerase, when present in the plant material and under certain conditions, catalyzes the formation of trans-2-hexenal from the cis-3-hexen-1-al. Cis-3-hexen-1-ol and other green note alcohols are then formed by the action of alcohol dehydrogenase (ADH), which reduces the aldehydes to alcohols. When this biosynthetic process is used commercially, ADH is often provided by the addition of live yeast, which naturally produces ADH. A disadvantage of using live yeast is that yeast naturally produces the enzyme enolase. Enolase interferes with the reduction reaction catalyzed by ADH, thus decreasing the efficiency of the reaction and the final yield of desired alcohol.

It would be highly desirable to provide an efficient and effective method for biosynthetically producing natural green note compounds in the absence of yeast, and additionally desirable to provide a microorganism capable of producing alcohol dehydrogenase to facilitate the green note production.

SUMMARY OF THE INVENTION

The present invention relates to the process of biosynthetically producing natural green note compounds, and the use of an active non-yeast mold capable of producing alcohol dehydrogenase (ADH), instead of live yeast. Accordingly, the present invention provides a non-yeast mold microorganism that is capable of producing alcohol dehydrogenase (ADH). In one preferred embodiment, the mold is obtained from the kale plant, and in a more preferred embodiment, is the strain *Geotrichium candidum* IMI 369326.

The present invention also provides a process for the conversion of a leaf aldehyde to a leaf alcohol, comprising contacting the leaf aldehyde with a microorganism capable of producing alcohol dehydrogenase, whereby the microorganism is a non-yeast mold derived from the kale plant, and under conditions sufficient to support the conversion reaction. In one preferred embodiment of the present invention, the microorganism is derived from the kale plant, and in a more preferred embodiment, is the strain *Geotrichium candidum* IMI 369326.

The present invention also relates to a method for providing green note compounds. The process, in one aspect, involves the steps of providing at least one unsaturated fatty acid, plant biomass having active levels of lipoxygenase and hydroperoxide lyase enzymes, and active alcohol dehydrogenase in the form of a non-yeast mold capable of producing alcohol dehydrogenase. These components are provided as a mixture by simultaneously contacting the fatty acid, plant biomass and alcohol dehydrogenase in the presence of an aqueous liquid under conditions sufficient to release lipoxygenase and hydroperoxide lyase from the plant biomass, and allow reaction of the fatty acid with the lipoxygenase, hydroperoxide lyase and alcohol dehydrogenase to provide green note compounds. After the mixture is reacted, the aqueous phase containing green note compound is collected and the green note compound separated from the aqueous phase.

The plant biomass (i.e. plant material), unsaturated fatty acid and alcohol, dehydrogenase are combined in the presence of an aqueous liquid. The ingredients are most preferably contacted with one another in an essentially simultaneous fashion; or the plant material is combined with a mixture of unsaturated fatty acid, a non-yeast mold that produces ADH, and water. Thus, the unsaturated fatty acid is converted to a green note compound. That is, the lipoxygenase and fatty acid interact to form a fatty acid hydroperoxide, which is cleaved by the action of the hydroperoxide lyase to form an aldehyde, which is converted to an alcohol by the action of the alcohol dehydrogenase, provided by the mold. Green note compounds produced according to the process steps of this aspect of the present invention include cis-3-hexenol as the primary green note compound component.

Green note compounds are used commercially to sharpen and enhance organoleptic properties in food (e.g., fruit flavorings) and perfumes (e.g., grassy or fresh scents). Accordingly, the green note compounds produced by the present invention are useful in the perfume and flavor industries.

DETAILED DESCRIPTION OF THE INVENTION

As summarized above, the present invention provides a method for producing natural green note compounds in the absence of yeast. Accordingly, one aspect of the present invention is an active mold that has the capability of converting a leaf aldehyde (i.e., trans-2-hexenal) to a leaf alcohol (i.e. cis-3-hexen-1-ol, or cis-3-hexenol). The active mold is a source of alcohol dehydrogenase (ADH) and the coenzyme nicotine adenine dinucleotide (NADH), which is involved in a reduction reaction that converts the aldehyde to the alcohol.

The mold is preferably isolated from kale plant material. As used herein, the term "kale plant material" includes any parts of the kale plant, mature or immature kale plants, juices or extracts of the kale plant, and kale in its processed or unprocessed form. In one preferred embodiment of the present invention, the microorganism is a strain of *Geotrichium candidum*, identified as IMI No. 369326. A deposit of this microorganism was submitted to the International Mycological Institute (IMI) on Oct. 30, 1995. Upon receipt by IMI, the microorganism was analyzed, given the identification name Geotrichum candidum 369326 and deposited in the IMI dried reference collection. The International Mycological Institute has the status of an international depository authority (IDA) under the Budapest Treaty on the International Recognition of the Deposit of Microorganisms for the Purposes of Patent Procedure. The International Mycological institute is located at the following address: Bakeham Lane, Englefield Green, Egham, Surrey TW20 9TY, United Kingdom. This species is the conidial stage of *Galactomyces geotrichium*, and is a member of the ascomycete order Endomycetales. See G. S. de Hoog et al., *Studies in Mycology* 29, 1–131 (1986).

In view of the foregoing, the present invention also provides a method of converting a leaf aldehyde to a leaf alcohol using a microorganism capable of such a conversion. Specifically, a leaf aldehyde is contacted with a microorganism capable of producing alcohol dehydrogenase (ADH), under conditions sufficient to support the conversion reaction. In one preferred embodiment of the present invention, the microorganism is derived from the kale plant, and in a more preferred embodiment, is the strain *Geotrichium candidum* IMI 369326. In the practice of the present invention, the ADH-producing mold most preferably is provided as a suspension, although it may also be provided in dried or lyophilized form.

The present invention additionally provides a method of producing green note or leaf alcohols via the reduction of green note aldehydes. In one embodiment of the invention, the green note aldehydes are produced by the enzymatic oxidation of a fatty acid substrate. It will be noted that in some green note processing, the production of both green note aldehydes and green note alcohols are desired, with the final result of the process being a mixture of the alcohol and the aldehyde. Therefore, in another embodiment of the invention, green note aldehydes are produced by the enzymatic oxidation of a fatty acid substrate, and a portion of the aldehyde is reduced to form the corresponding alcohol, while the remaining portion of the aldehyde product is retained in its original form. The proportion of alcohol to aldehyde produced may be controlled by varying the amount of ADH-producing non-yeast mold, or by varying the amount of any other of the enzymes used in the process (e.g., lipoxygenase, hydroperoxide lyase, and aldehyde isomerase).

Accordingly, green note compounds capable of being provided using the process of the present invention can vary. Exemplary compounds include cis-3-hexen-ol, trans-2-hexen-1-ol, trans-3-hexen-1-ol, 1-hexanol, cis-3-penten-3-ol and cis-2-penen-1-ol, trans-2-hexenal, and cis-3-hexen-1-al, with cis-3-hexen-1-ol and trans-2-hexenol being preferred. When the fatty acid is linolenic acid, and all of the ingredients are combined in an essentially simultaneous fashion, the green note compounds consist primarily of cis-3-hexen-1-ol; and depending on the purity of that acid, (i.e. the presence of certain amounts of other fatty acids), relatively minor amounts of other green note compounds (e.g. 1-hexanol) can be produced. When the ADH is combined with the ingredients after the other ingredients have been combined, the green note compounds which result have a tendency to consist of complex mixtures of green note compounds, which mixtures can vary depending upon factors such as selection of fatty acid, amount of mold employed, and timing of mold addition to the other ingredients of the biochemical reaction. Typical green note compounds are volatile, and are highly flavorful and aromatic. Desired green note compounds are those which exhibit fresh, green, and leafy aroma and flavor properties and characteristics.

Plant materials useful in carrying out the process of the present invention can vary. Plants having relatively highly accessible amounts of enzymes (e.g., lipoxygenase and hydroperoxide lyase) are preferred. The plant material can also contain aldehyde isomerase enzyme, which has the effect of transforming an aldehyde in a cis-form to a trans-form. Plants materials such as alfalfa have relatively high levels of aldehyde isomerase, while plant materials such as watermelon foliage have relatively low levels of aldehyde isomerase. The plant material can be provided by a single plant variety or by a mixture of two or more plant types, each of which has a desirable level of lipoxygenase, hydroperoxide lyase or aldehyde isomerase. If desired, various portions of different types of plants can be mixed together (e.g., fruit from at least one type of plants can be combined with foliage of at least one other type of plants ). It is also desirable to select plants that do not provide undesirable flavor or aroma characteristics to the ultimate green note composition which is isolated.

Representative plant materials are set forth by Hatanaka, *Bull. Inst. Chem. Res., Kyoto Univ.*, Vol. 61, p. 180 (1983); Sekiya et al., *Phytochem.*, Vol. 22, p. 1869 (1983); Hatanaka et al., ACS Symposium Biogeneration of Aromas (1985); Gotz-Schmidt et al., *Lebensm. Wiss. Tech.*, Vol. 19, p. 152 (1986). Desirable plant materials which incorporate hydroperoxide lyase and/or lipoxygenase enzymes include vegetative growth or foliage (e.g., seedlings, leaves and vines) of cantaloupe (*Cucumis melo*) (e.g., cvs. 'Hale's Best Jumbo', 'HMX Western', 'Hearts of Gold'), watermelon (*Citrullus lanatus*) (e.g., cvs. 'Charleston Gray', 'Crimson Sweet', 'Sugar Baby', 'Sultan'), strawberry (*Fragaria Xananassa*), cucumber (*Cucumis saetivus*), kidney bean (*Phaseolus vulgaris*), tomato (*Lycopersicon lycopersicum*), honeydew melon (*Cucumis melo*) (e.g., cvs. 'Morning Ice') and amaranths (*Amaranthus*) (e.g., pigweed foliage, such as *Amaranthus retroflexus*); the leaves or tops of radish (*Raphanus sativus*); alfalfa (*Medicago satira*); kidney bean (*Phaseolus vulgaris*), hanover salad (*Brassica napus*), rutabaga (*Brassica napus*), spinach (*Spinacia oleracea*), turnip (*Brassica rata*), Chinese cabbage (*Brassica rapa*) (e.g., cvs. 'Pe-Tsai'), mustard (*Brassica juncea*) (e.g., 'Florida Broadleaf', 'Old Fashion'), salad greens or mixed greens (e.g., mixtures of turnip, mustard, kale, and the like), false acacia (*Robinia pseudoacacia*), clary sage (*Salvia sclarea*) and tea (*Thea sinensis*); and the fruit or seed of soybean, green bean, strawberry, kidney bean or snap bean; and processed plant materials such as soy flour. The most desirable plant materials are those that combine high levels of enzyme activity and high biomass potential; and are adaptable to standard agronomic production methods and processing conditions.

The unsaturated fatty acid can vary. The unsaturated fatty acid is provided in a free acid form (e.g., in a carboxylic acid or salt form). Examples are oleic acid, linoleic acid, linolenic acid (alpha and gamma forms), arachidonic acid, eicosapentaenoic acid, ricinoleic acid, and the like. The unsaturated fatty acid can also be provided by reacting an oil (e.g., vegetable oils such as linseed oil, safflower oil and soya oil) with a lipase or using high pressure steam hydrolysis conditions to hydrolyze triacylglycerols in that oil to free fatty acid and glycerol. See, for example, U.S. Pat. No. 4,769,243 to Kanisawa et al., the disclosure of which is incorporated herein by reference in its entirety. Unsaturated fatty acids also can be provided by chemical saponification of fats and oils using base. Techniques for providing unsaturated fatty acids from fats and oils will be readily apparent to the skilled artisan. The unsaturated fatty acid can be employed as a mixture of acids (i.e., as a formulation of relatively low purity of one particular fatty acid). However, the unsaturated fatty acid can also be employed in a relatively pure form (e.g., having a purity of greater than about 90 weight percent, preferably greater than about 95 weight percent, and more preferably greater than about 97 weight percent). Unsaturated fatty acids of high purity tend to provide green note alcohols of high purity. For example, linolenic acid of high purity tends to yield a green note composition that is high in purity of cis-3-hexen-1-ol.

The amount of unsaturated fatty acid relative to the amount of plant material can vary, and depends upon factors such as the level of enzyme in the plant material. Typically, amounts of acid are in slight excess to the enzyme level in the plant material. For example, for linolenic acid, the amount of acid ranges preferably from about 5 to about 10 mg, and more preferably from about 7 to about 9 mg linolenic acid per gram of plant material.

An active non-yeast mold is provided by the present invention. The active or fresh mold has the capability of converting an aldehyde to an alcohol. The mold is a source of alcohol dehydrogenase (ADH) and the coenzyme nicotine adenine dinucleotide (NADH), which provides biological reducing power (i.e. and ability to cause a conversion of an aldehyde to an alcohol). An example of a suitable mold is *Geotrichium candidum* IMI 369326, described above. The mold is preferably provided as a suspension, but may be provided in wet cake form or in dried or lyophilized form. If desired, the mold may be combined with additional materials such as sugars (e.g. glucose) in an amount sufficient to enhance the enzymatic activity of the ADH. The mold is employed in order to provide a source of ADH which causes reduction of the aldehydes formed by the production of hydroperoxide lyase to the corresponding alcohol.

The amount of mold added to the mixture can vary, and will depend on the desired transformation of aldehyde to alcohol. For example, an excess of mold can be employed in order to provide for nearly complete conversion of aldehyde to alcohol. Normally, the amount, by weight, of mold employed does not exceed 30 times, and preferably is about 15 to about 20 times, that of the amount of the unsaturated fatty acid employed.

The unsaturated fatty acid, plant material and mold are mixed or otherwise blended together homogeneously in the presence of an aqueous liquid. Such a liquid consists primarily of water, normally greater than about 90 weight percent water, and can be essentially pure water in certain circumstances. For example, a solvent having an aqueous character can be distilled water, tap water, or the like. However, a solvent having an aqueous character can include water having substances such as pH buffers, pH adjusters, organic and inorganic salts, sugars, amino acids or surfactants incorporated therein. The solvent also can be a co-solvent mixture of water and minor amounts of one or more solvents which are miscible therewith (e.g., various alcohols, polyols, and the like).

Typically, the aqueous liquid is provided at a temperature of about 10° C. to about 25° C. The plant material can be chopped (e.g., to a size of about 7 centimeters by about 7 centimeters, or to a size as large as about 14 centimeters by about 28 centimeters) immediately prior to the aforementioned blending. Such chopping or subdivision insures accurate addition of plant biomass to the shearing device in a commercial scale process when equipment such as a weigh-belt feeder is employed. However, the degree of chopping is not so great in order that the cellular disruption of the biomass is not significant and the enzymes do not experience an undesirable release from the biomass prior to the time that such enzymes are desired to be used. As such, the enzymes are active when contacted with the fatty acid in order to carry out the biochemical reaction upon the fatty acid. Active enzymes have the ability to cause bioreaction upon the fatty acid. High levels of active enzymes are desirable, such that a large amount of fatty acid may undergo the desired bioreaction. Enzymes within the cells of the biomass tend to become inactivated very rapidly upon release from those cells as a result of action of oxidation, proteases, and other inhibitors present within the plant material.

In the preferred aspect of the present invention, all of the ingredient materials are added together simultaneously, as opposed to a step-wise fashion. That is, in within a matter of seconds, the plant material is combined with the fatty acid and mold in an aqueous slurry. Alternatively, the plant material, fatty acid and mold are combined at essentially the same time in an aqueous environment. In a continuous process, the fatty acid, plant material and mold are metered into a mixing region along with the aqueous liquid in controlled amounts under conditions such that the desired enzymes are released from the plant material and such that the biochemical reaction can occur. As such, the enzymes are released from the plant material in the presence of the mold and in the presence of the unsaturated fatty acid. As a result, green note compounds predominantly having a cis-3-hexen-1-ol character and type are formed. In contrast, when the mold is added to the aqueous slurry of plant material and unsaturated fatty acid after the reaction of enzymes in the slurry has been initiated, the resulting green note compounds consist of mixtures of significant amounts of green note aldehydes and alcohols.

Typically, the reaction mixture is maintained above 15° C., and preferably above about 20° C. It is desirable to maintain the mixture below 45° C., and most desirably below 40° C. in order to ensure significant activity of the lipoxygenase and hydroperoxide lyase. Preferably, the mixture is maintained at a temperature which does not exceed about 35° C., and most preferably is below about 30° C.

The amount of aqueous liquid employed can vary. The amount of aqueous liquid is employed in an amount sufficient to provide for ease of shearing and hence minimize temperature increases that potentially provide an attendant destruction or inactivation of the enzymes. However, it is also desirable to maintain the amount of aqueous liquid sufficiently low in order to allow for greater ease in later processing steps when the ultimate green note product is separated from that liquid for isolation. Ratios of aqueous liquid to plant material can range from about 2:1 to about 7:1, preferably from about 3:1 to about 6:1, and more preferably about 5:1.

Cell disruption conditions are provided in order to facilitate release of lipoxygenase from the water soluble fraction of the cytoplasmic region of the cells which make up the biomass, and hydroperoxide lyase from the chloroplast membrane region of the cells which make up the biomass. Cell disruption most preferably is provided by shearing action. That is, shearing provides a maceration of the cell to expose the enzymes, and also provides rapid release of the enzymes from the cell material in order to effectively provide the enzymes in an environment for the desired reaction. Cellular disruption or tissue disruption resulting from the action of high shear exposes the intracellular enzymes of the biomass to the fatty acid and the active non-yeast mold in an essentially instantaneous fashion. Shearing provides rapid release of the lipoxygenase and hydroperoxide lyase enzymes from the plant material in order that those enzymes can react with the fatty acid to efficiently produce cis-3 hexenal, which is in turn converted to cis-3-hexen-1-ol by the alcohol dehydrogenase.

By shearing or high shear is meant rapid agitation of the processed slurry in order to provide or approach homogenization of that slurry. Shearing can be provided by fast moving mixer blades (e.g., moving in excess of about 3000 rpm) or having high blade tip speeds (i.e., in excess of about 9000 ft./second). Shearing conditions are sufficient to subject the total volume of the slurry being processed to conditions of shear stress and strain. In a continuously fed high shear device, such as a Reitz disintegrator, cell disruption can be carried out in less than about 30 seconds, often in less than about 15 seconds, while total shear time typically is less than 5 minutes. In a batch-wise shearing device, such as a blender, the mixture typically is agitated for about 0.5 to about 5 minutes, usually about 1 to about 4 minutes. If desired, a surfactant (e.g., Lecithin or Tween 20) can be incorporated into the mixture during shearing in order to assist in release of the hydroperoxide lyase from the chloroplasts of the cells of the plant material and to assist in improving the oil/water interface of the enzyme with fatty acid. Shearing can be carried out using high shear kitchen-type blenders (e.g., a Waring blender), a Reitz Mill, a Reitz Disintegrator, a Fitzmill mixer, a Hobart mixer, a Breddo mixer, or like high shear mixing devices; an ultrasonic mixing device; or an impaction and attrition device such as a Kady Mill. It may also be desirable to couple two mixing devices, such as a Reitz disintegrator and a Kady Mill or a Reitz disintegrator and a Breddo mixer, to provide optimal shearing resulting in maximal contact of unsaturated fatty acid and released enzymes. Such high shear devices provide rapid maceration of the plant material so as to provide rapid and maximum release of the enzymes under aerated conditions, and also provide for conditions of rapid interaction (i.e., mixing) of the components of the reaction mixture.

The liquid and pulp portions of the resulting mixture are separated from one another. Separation of pulp and other solids from the aqueous liquid acts to facilitate removal of green note compounds from the aqueous liquid. Centrifugation (e.g., using a disc-stack, decanter, or similar device) can be employed. Filtration (e.g., using a rotary vacuum filter, or similar device) can be employed. Typically, such separation is carried out by screening water insoluble solids from the aqueous liquid. Screening or dewatering devices include a Sweco screen, a Rotex screen or a Hydrosieve. If desired, the mixture can be pressed to remove a further amount of the liquid portion from pulp portion. A Reitz Press or similar equipment can be used to further separate the liquid and pulp portions from one another. As such, aqueous liquid containing green note compound is collected.

The liquid portion is allowed to undergo a reaction, set or incubation time. During such time, the reaction mixture can be allowed to set for an extended period without mixing or agitation, or the mixture can be agitated. Preferably, the shearing (i.e., plant tissue disruption) and extended set (i.e., reaction) periods are carried out under ambient atmosphere and at temperatures which approximate ambient temperature. The reaction time typically lasts at least 15 minutes, often ranges from about 20 to about 30 minutes, frequently does not exceed about 6 hours, and usually does not exceed about 60 minutes. Conditions of temperature and pH of the liquid can be controlled during the extended reaction time, however, the temperature is often ambient temperature and the pH is not altered after the mixing period. The extended reaction step can be carried out without purposefully aerating the mixture, without introducing supplemental oxygen into the mixture, or without carrying out the process steps under inert (e.g., nitrogen) atmosphere. Typically, the initial shearing action which is provided in ambient atmosphere allows for adequate introduction of oxygen into the mixture.

The green note compounds which are within the aqueous liquid are separated from the aqueous liquid and most preferably are isolated. That is, the green note compounds are provided in a relatively concentrated or essentially pure form. Green note compounds can be isolated so as to have purities of greater than about 90, often greater than about 95, frequently greater than about 98, and even greater than about 99 percent, on a weight basis. The manner in which the green note compounds are separated from a significant amount of the aqueous liquid in which it is provided can vary.

The aqueous liquid containing the green note compounds can be subjected to distillation so as to obtain a distillate containing green note compounds. Such distillation techniques typically involve distilling the aqueous liquid under vacuum (e.g., at 25° C. to 60° C., and 10 to 150 mm Hg). In such a manner, collection as distillate of about ⅓ or more of the volume of the liquid which is subjected to distillation typically provides within the distillate greater than 98 percent of the green note compounds present in the starting liquid. For example, collection of distillate of about ½ of the volume of the aqueous liquid subjected to rotary vacuum distillation at 55° C. and 15 mm Hg typically provides essentially all of the green note compounds subjected to distillation as distillate. Under such conditions, the distillate is a mixture of green note compounds and water, and the green note compounds frequently are present in the water in an amount of about 500 ppm. The condensate so provided can be passed through a collection column (e.g., a column containing particles of activated carbon, or a column containing hydrophobic macroporous ion exchange resin particles such as Amberlite XAD-2 from Rohm & Haas) so that green note compounds are collected on the substrate material within the column. The green note compounds then can be removed from the collection column using an eluting solvent (e.g., ethyl acetate, diethyl ether, hexane, chloroform, methanol or ethanol); and isolated to a desired purity by fractional distillation techniques (e.g., ambient, vacuum or steam distillation techniques) using a high efficiency distillation column. A mixture of ethanol, water and green note compound can be distilled so as to provide fractional distillation, and hence separation of the green note compound from the other liquids. Alternatively, the green note compound can be removed from the collection column using a supercritical fluid (e.g., supercritical carbon dioxide at 38° C. to 45° C., and 340 to 400 bar pressure); and isolated to high purity by evaporating liquid carbon dioxide under ambient pressure conditions. Alternatively, the green note compound can be removed from the collection column using thermal desorption techniques, and isolated by condensing the vaporized compound.

The process of the present invention provides an efficient and effective method for producing green note compounds at relatively high yield and of high purity. The process of the present invention provides an advantage over conventional, yeast-utilizing methods in that the non-yeast mold of the present invention does not produce enolase during the aldehyde-to-alcohol reduction reaction. Accordingly, the desired green note alcohols are produced in higher field with the present invention.

In addition to utility in green note processing, the non-yeast mold of the present invention is useful in any alcohol fermentation process that requires or utilizes alcohol dehydrogenase (ADH). Many of these processes typically utilize yeast as the biological source for ADH. Therefore, the non-yeast mold of the present invention may be used as a yeast substitute in processes for the preparation of alcoholic beverages, such as beer, wine, and distilled spirits. Additionally, the mold can be used as a yeast substitute in processes used to provide alcohols for industrial uses (e.g., solvents, substrates for the synthesis of numerous other organic compounds, and preparations of fuel products such as the gasoline supplement "gasohol").

The present invention is more fully illustrated by the following examples, which are set forth to illustrate the present invention and are not to be construed as limiting thereof. In the following examples, L means liters, mL means milliliters, rpm means revolutions per minute, and all temperatures are in degrees Centigrade.

EXAMPLE 1

During normal trans-2-hexenal (leaf aldehyde) production, the appearance of cis-3-hexenol (leaf alcohol) is observed. To determine the causal agent responsible for the conversion of cis-3-hexenal to cis-3-hexenol in the absence of added yeast, several green note samples from kale plants are collected for microbial evaluation over a period of four months. The collected examples include kale juice removed from the site where grinding of the plant material occurs, and tanks in which plant material is stored. Microbial samples are collected by serial dilution techniques, as well as by the streak method.

Potato dextrose agar media is used to enumerate the mold count. The plates are incubated at room temperature for 48 hours and are evaluated quantitatively. One particular white mold is consistently isolated from ten different samples (average colony forming unit is $10^5$/mL), each collected on a different day. The mold is purified by single spore isolation and is maintained on potato dextrose agar slants.

For comparative studies, the mold is fermented in 1 L potato dextrose broth in conical flasks. The flasks are incubated in a shaker at 26° C. for 1 week. The filtrate and the pellet are separated using a centrifuge (3000 rpm for 10 minute at 10° C.). The mold is screened for ADH enzyme production by using the standard green note reaction. The results indicate strong ADH production by the isolated mold that is superior to the standard yeast ADH production conventionally used for green note (cis-3-hexenol) production.

A sample of the isolated mold was sent to the International Mycological Institute, where it was assigned the deposit number IMI 369326, and identified as a strain of the species *Geotrichium candidum*.

In the specification and examples, there have been disclosed preferred embodiments of the invention. Although specific terms are employed in these examples, they are used in a generic and descriptive sense only and not for the purpose of limitation, the scope of the invention being defined by the following claims.

That which is claimed is:

1. An isolated microorganism, wherein said microorganism is a mold which produces alcohol dehydrogenase, and said microorganism is *Geotrichum candidum* IMI 369326.

2. A biologically pure culture for converting leaf aldehydes to leaf alcohols consisting of the microorganism according to claim 1.

3. A process for the conversion of a leaf aldehyde to a leaf alcohol, comprising contacting the leaf aldehyde with a microorganism which produces alcohol dehydrogenase, whereby the microorganism is the non-yeast mold *Geotrichum candidum* IMI 369326, under conditions sufficient to support the conversion reaction.

4. A method of providing a green note compound, comprising the steps of:

(a) contacting at least one unsaturated fatty acid, plant biomass having active levels of lipoxygenase and hydroperoxide lyase enzymes, and the non-yeast mold *Geotrichum candidum* IMI 369326 which produces alcohol dehydrogenase in the presence of an aqueous liquid under conditions sufficient to:
      (i) provide release of lipoxygenase and hydroperoxide lyase from the plant biomass, and
      (ii) provide reaction of the fatty acid with the lipoxygenase, hydroperoxide lyase and alcohol dehydrogenase to provide green note compound;

(b) collecting the aqueous phase containing green note compound; and (c) separating green note compound from the aqueous phase.

5. The method according to claim 4, whereby the non-yeast mold of step (a) is contacted simultaneously with the fatty acid and the plant biomass.

6. The method according to claim 4, whereby the non-yeast mold of step (a) is contacted with the fatty acid and plant biomass at least 5 minutes after the fatty acid and plant biomass have begun to react.

7. The method according to claim 4 whereby the non-yeast mold of step (a) is derived from kale.

8. The method according to claim 4 whereby the fatty acid is linolenic acid.

9. The method according to claim 4 whereby the green note compound separated in step (c) is selected from the group consisting of cis-3-hexen-ol, trans-2-hexen-1-ol, trans-3-hexen-1-ol, 1-hexanol, cis-3-penten-3-ol and cis-2-penen-1-ol.

10. The method according to claim 4, whereby the plant biomass of step (a) consists essentially of alfalfa.

11. The method according to claim 4, whereby said collection step (b) is performed on an ion-exchange resin.

* * * * *